United States Patent [19]

Oxford

[11] 4,132,585
[45] Jan. 2, 1979

[54] METHOD OF AUTOMATICALLY MONITORING AND REGENERATING AN ETCHANT

[76] Inventor: Keith E. Oxford, 4010 Paducah Dr., San Diego, Calif. 92117

[21] Appl. No.: 784,237

[22] Filed: Apr. 4, 1977

Related U.S. Application Data

[62] Division of Ser. No. 614,072, Sep. 17, 1975, abandoned.

[51] Int. Cl.[2] .................. C23F 1/00; G01N 21/26
[52] U.S. Cl. ............................ 156/626; 156/642; 356/433; 356/434; 356/442
[58] Field of Search .................. 156/626, 642, 627; 137/2, 4; 356/204, 208, 205, 206; 250/576

[56] References Cited

U.S. PATENT DOCUMENTS

| | | | |
|---|---|---|---|
| 3,592,715 | 7/1971 | Lindstrom | 156/626 |
| 3,607,549 | 9/1971 | Bielefeld et al. | 156/642 |
| 3,690,833 | 9/1972 | Ferrari | 250/576 |
| 3,705,061 | 12/1972 | King | 156/642 |
| 3,816,306 | 6/1974 | Roy | 156/642 |
| 3,964,956 | 6/1976 | Snyder | 156/626 |
| 3,980,517 | 9/1976 | MacTaggart | 356/208 |
| 4,042,444 | 8/1977 | Snyder | 156/642 |
| 4,058,431 | 11/1977 | Haas | 156/626 |

*Primary Examiner*—Jerome W. Massie
*Attorney, Agent, or Firm*—Brown & Martin

[57] ABSTRACT

The composition of etchant solution withdrawn from an etcher is monitored to diagnose a component deficiency. A light sensor is responsive to the color density of light rays passing through the etchant. A meter relay is responsive to the light sensor and if the color density of the etchant falls outside preset levels a pump is energized causing addition of a constituent component into the etchant. A second light sensor senses the color density of the light rays passing through the etchant after the addition of the constituent component. A second meter relay is responsive to the second light sensor. If no improvement of the etchant color is detected, the second meter relay causes the discontinuance of the constituent component addition and switches to the addition of another constituent component.

8 Claims, 2 Drawing Figures

METHOD OF AUTOMATICALLY MONITORING AND REGENERATING AN ETCHANT

This is a division, of application, Ser. No. 614,072, filed Sept. 17, 1975, now abandoned.

BACKGROUND OF THE INVENTION

Etching of copper workpieces is generally accomplished in etching machines wherein the workpiece is placed on a conveyor and is transported into the etching machine for exposure to an industrial etchant. A commonly used etchant is a solution of cupric chloride. Although cupric chloride and other etchants are quite effective in etching metal from the workpiece, the etching procedure becomes gradually less efficient. There is a continuous reduction of the cupric ($Cu^{+2}$) to cuprous ($Cu^{+1}$) ions. Cuprous ions are totally ineffective as an etchant and have a tendency to retard the etching procedure. As the etching procedure continues, the concentration of copper in solution increases. This causes the concentration of cuprous ions to increase and results in a further decrease in the etching efficiency or speed. Thus, the continuous accretion of copper into the etching solution reduces the ability of the etchant to efficiently perform its functions.

Some etchants, particularly cupric chloride, change color as the etchant vigor deteriorates. A fresh solution of cupric chloride is a clear green color, but a spent solution, containing a substantial amount of cuprous chloride, turns brown because cuprous chloride, being insoluable, forms a brownish precipitate.

To compensate for the gradual degradation of etching efficiency, prior art systems have adopted methods to regenerate the etchant. Regeneration means that one component, such as copper, may be extracted and the fluid may be recycled through the etcher. Regeneration may also be accomplished by the addition of acid and oxidizer to reoxidize the cuprous chloride back to cupric chloride. The reoxidization regenerates the etchant to increase its vigor as an etchant.

The regenerative approach, in the prior art, has proven to be relatively costly. It requires investment in expensive apparatus. Furthermore, the components of regenerative systems occupy a very large part of the production space of industrial installations. Regenerative systems have been relatively complex and require frequent and careful maintenance. Many industrial installations are subject to variable or irregular work loads, and in such systems, the conventional regenerative approaches are of minimum assistance. Furthermore, where there is substantial variability in the work load, large portions of the regenerative components may be unused for extended periods of time.

There has been a need, therefore, to provide a regenerative system that efficiently regenerates the etchant so that it will efficiently etch production workpieces. There has also been a need for a regenerative system that continuously monitors the etchant composition and detects deterioration of the etchant. Furthermore, there has been a need for an effective regenerative system that is compact and relatively inexpensive.

SUMMARY OF THE INVENTION

In an exemplary embodiment of the invention, as the etching machine begins operation, etchant is sampled in a pipe connected to the monitoring apparatus. A flow detector means detects etchant flow and enables a time delay means that turns on the system. The time delay is for the purpose of expunging bubbles and precipitants from the systems. A light sensing means in the form of cadmium sulfide sensor senses the color density of the etchant. In the event that the color density falls within prescribed limits, no action is initiated. If however, the color density does not fall within the prescribed parameters, a first monitoring means, in the form of a meter relay, enables a pumping means and injects a constituent component into the system. The constituent component may be acid or a salt-oxidizer. The constituent component initially chosen will be that same component that cured the system the previous time a deficiency was detected.

Second monitoring means, in a form of a second meter relay means, is similarly provided with a second light sensing means such as an identical cadmium sulfide detector. The first light sensing means senses the color density of the etchant upstream of a reaction chamber prior to the addition of a curing constituent component. The second light sensing means senses the color density of the etchant downstream, after the curing constituent component has been added in a reaction chamber.

The first meter relay means is present to be more sensitive than the second meter relay. This means that the second meter relay in effect calls for a constituent component addition before the first meter relay permits the addition of that component. The second meter relay enables a timing means that times out a predetermined interval. If during that interval, the second meter relay senses a cure in the deficiency of the etchant, the timer means is disenabled. If however, the second meter relay senses no curing after the passage of the preset time interval, the timer enables a latching relay that switches from the addition of the one component to another component for the purpose of curing the deficiency in the etchant. Having now chosen the curing component, the second meter relay disenables the timer. The apparatus remains in the curing component addition mode until a sufficient amount of that curing component has been added such that the color density of the etchant falls within the prescribed parameters. When the first meter relay senses the change in color density to within the prescribed parameters, it breaks the circuit to the pumping means and no additional curing components are added to the system.

The first meter relay maintains a continuous monitoring of the solution and is effective to cycle the system on and off as necessary according to the condition of the etchant. Each time the etchant registers a deficiency that causes the color density to fall outside the prescribed parameters, the first monitoring means causes the system to run through its prescribed cycle to cure the deficiency by adding a curing constituent component.

It is therefore an object of the invention to provide a new and improved method and apparatus for regenerating etchant in an etching machine.

Another object of the invention is to provide a new and improved method and apparatus for continuously monitoring etchant composition.

Another object of the invention is to provide a new and improved method and apparatus to continuously monitor etchant composition and to determine the existance of a constituent component deficiency in the etchant.

Another object of the invention is to provide a new and improved method and apparatus to determine which constituent component is deficient.

Another object of the invention is to provide a new and improved method and apparatus to introduce a component that cures the etchant deficiency.

Another object of the invention is to provide a new and improved method and apparatus that switches from a non-curing component to a curing component.

Another object of the invention is to provide a new and improved method and apparatus that remains in the curing component addition mode until the etchant composition is sufficiently regenerated.

Another object of the invention is to provide a new and improved method and apparatus that continuously monitors the etchant composition by detecting color density changes of the etchant.

Another object of the invention is to provide a new and improved method and apparatus in which a switch is made form a non-curing to a curing compoent after a predetermined time delay in which the effects of component addition are monitored.

Another object of the invention is to provide a new and improved method and apparatus that bleeds excess etchant that builds up due to component addition.

Another object of the invention is to provide a new and improved method and apparatus that delays the operation of the apparatus until a specified period after flow is detected in the etching machine.

Another object of the invention is to provide a new and improved method and apparatus that is compact, reliable and continuous in operation.

Another object of the invention is to provide a new and improved method and apparatus that utilizes little energy yet maintains a constant vigilance over the etchant.

Other objects and many attendant advantages of the invention will become more apparent upon a reading of the following detailed description together with the drawings in which like reference numerals refer to like parts throughout and in which.

DETAILED DESCRIPTION OF THE DRAWINGS

Figure 1:
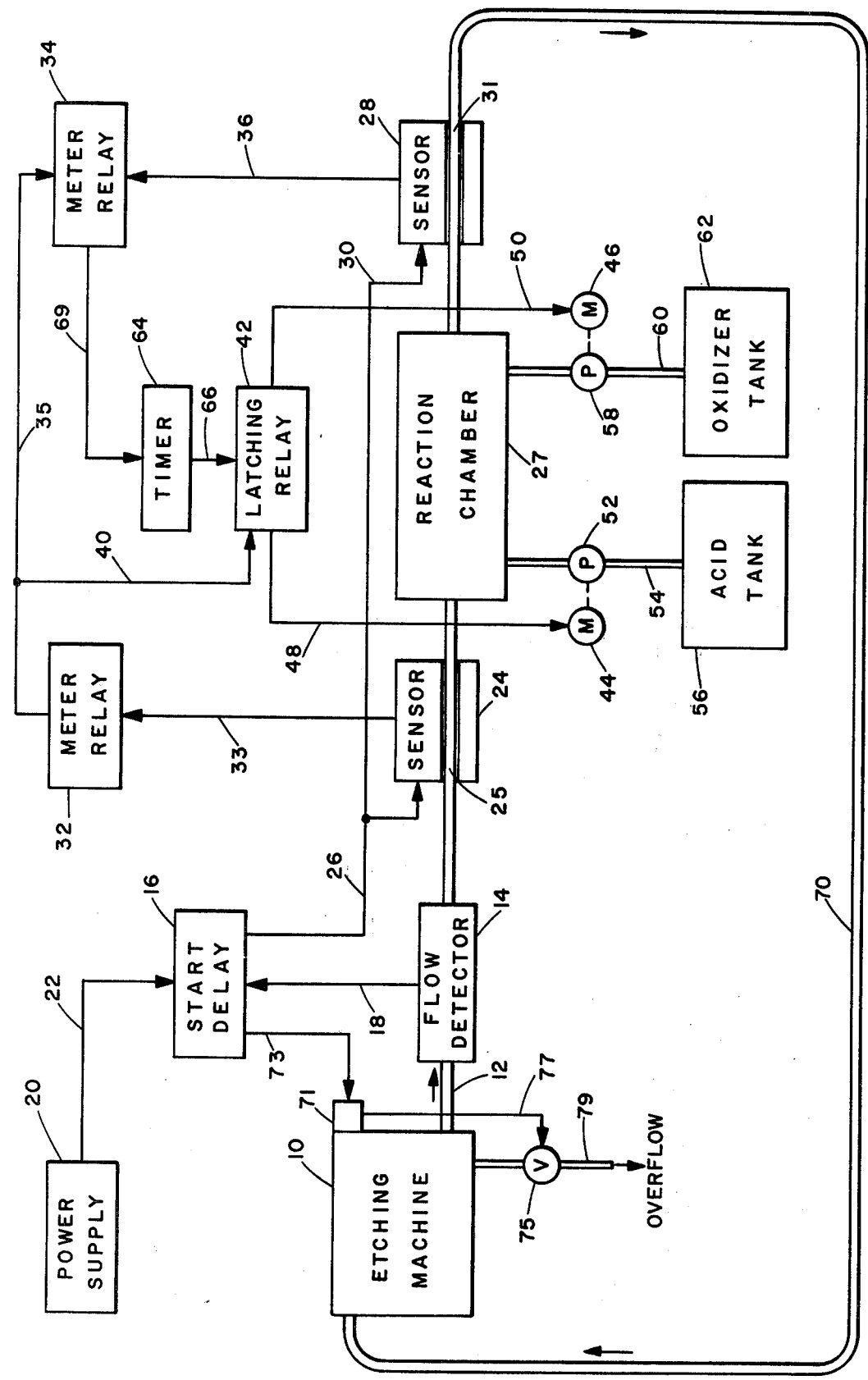
FIG. 1 is a diagram of the monitoring apparatus.

In an exemplary embodiment of the invention, the apparatus is used in conjunction with an etching machine 10 that etches parts passing into the machine by means of a conveyor (not shown). The apparatus may be utilized with a variety of etchants so long as the etchant turns color as it loses its vigor. For instance, cupric chloride, when etching copper, forms cuprous chloride and as such becomes rapidly ineffective as an etchant. Also, cuprous chloride being insoluable, forms a brownish precipitant as the etching process takes place. The chemical reaction causes change in color from clear green to murky brown. The apparatus will be described with reference to a cupric chloride etching system. However, it should be understood that with slight modifications the invention is adaptable for use with any etchant that produces a change in color as the vigor of the etchant is dissipated.

The cupric chloride etchant can lose its vigor due to deficiency of either acid or oxidizer. Therefore, the addition of an acid such as muriatic acid, and the addition of a solution such as sodium chlorate can regenerate the etchant to establish an acceptable vigor. Sodium chloride acts as a catalyst or buffering agent. With cupric chloride, a deficiency of either acid or oxidizer will cause a change in color from clear green to murky brown. Accordingly, it is the function of the apparatus to selectively add one or the other component to re-establish the operating vigor of the etchant.

Sample etchant is tapped from the etching machine 10 by means of the pipe 12. Flow detector means 14 in the form of a pressure switch detects the flow of etchant from the etching machine 10, as soon as the etching machine is started. If flow is detected, the flow detector 14 enables a start delay timer 16 via line 18. Power is supplied from the power supply 20, via line 22, to the start delay timer 16. The start delay timer 16 enables a first color sensor 24, via line 26. The color sensor 24, that may be in the form of a cadmium sulfide sensor monitors the color density of the etchant in pipe 25 upstream of a reaction chamber 27. The start delay timer 16 also enables a second color sensor 28, via line 30. The second color sensor 28 may also be a cadmium sulfide sensor and it functions to monitor the color density of the etchant in pipe 31 of the downstream side of the reaction chamber 27.

The first color sensor 24 enables a first meter relay means 32, via line 33. The first meter relay means 32 is preset to respond to color density changes of the etchant via changing resistance of color sensor 24. Specifically, when the color density monitored by the color sensor 24 falls outside prescribed parameters, the first meter relay 32 enables a second meter relay 34 via line 35. The second meter relay 34 is responsive to the second color sensor 28 via line 36. It should be understood that the second meter relay 34 performs no function until the etchant color density deteriorates sufficiently and the appropriate responsive action is taken by the first meter relay 32. If the first meter relay 32 detects a color density change that falls outside the prescribed parameters, then via line 40, latching relay 42 is energized. The latching relay 42 enables one or the other of the motors 44 and 46, via the lines 48 and 50 respectively. If the motor 44 is enabled, it operates a pump 52 that via pipe 54 supplies acid from the acid tank 56 to the reaction chamber 27. Alternatively, if motor 46 is enabled, it operates pump 58 that supplies oxidizer via pipe 60 from the oxidizer tank 62 to the reaction chamber 27. At the very first instant of color density deficiency detection, that motor 44 or 46 will operate that operated in the previous cycle.

A timer 64 is enabled by meter relay 34, via line 69 and times out a preset interval. If after the preset interval has passed, no curing color density change has been detected by meter relay 34, then the timer 64 causes the latching relay 42, via line 66 to switch over to the other motor 44 or 46 that in turn causes the other constituent component to be added to the reaction chamber 27. For instance, if in the previous constituent component addition mode, acid was the curing component, motor 44 is enabled and acid would be introduced into the reaction chamber 27. If after the predetermined time delay, the second meter relay 34 detected no color density change, the latching relay 42 would switch over to enable motor 46 causing the addition of oxidizer to the reaction chamber 27. The apparatus remains in the component addition mode until the first meter relay 32 senses a color density change falling within the prescribed parameters. When that occurs, the first meter relay disenables the second meter relay 34, the timer 64, the latching relay 42 and the motors 44 and 46. However, the first meter relay 32 maintains a continuous monitoring of the etchant and will cycle the apparatus on and off as often as it detects a color density change falling outside the prescribed parameters. The regenerated etchant flows through pipe 70 back into the etchaing apparatus and is continuously monitored by the color sensor 24 to detect any color changes. An overflow sensor 71 enabled via line 73 senses an excess of etchant in the etching machine 10, due to the addition of acid or oxidizer. The overflow sensor 71 enables a valve 75 via line 77 that controllably bleeds excess etchant via pipe 74.

Figure 2:
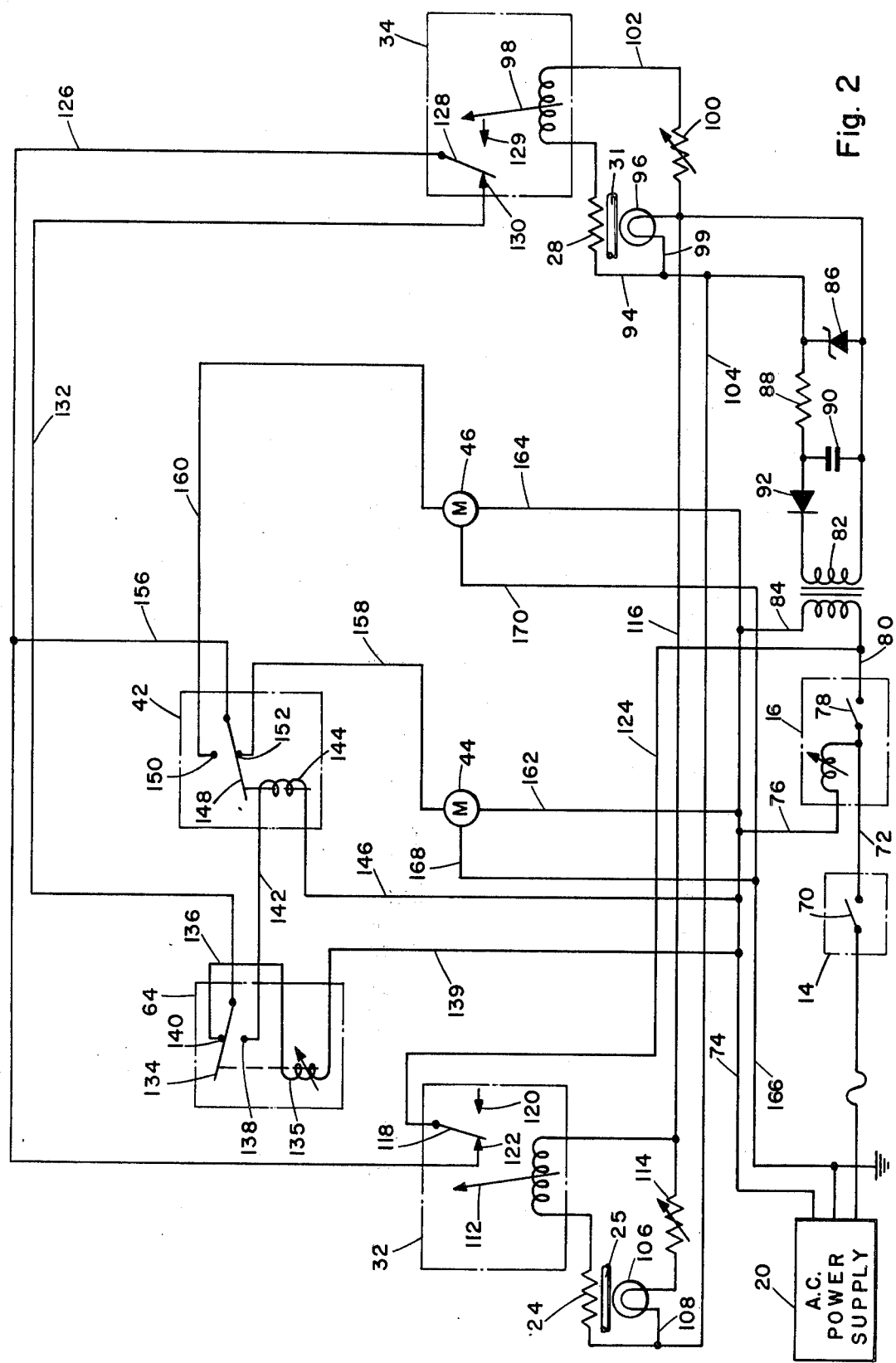
FIG. 2 is a schematic diagram of the electronic circuitry of the apparatus.

Turning now to FIG. 2, the operation of the various components will be more completely understood in conjunction with the electrical circuitry of the apparatus. No power flows from the AC power supply 20 to the system until the flow detector 14 senses etchant flow in the system. The flow detector 14 comprises a pressure switch 70. When the pressure switch 70 is closed, the start delay timer 16 is enabled via line 72. The start delay timer 16 is connected to the common line 74, via line 76. After the preset time interval has passed, the start delay timer 16 closes by closing switch 78. The switch 78 energizes line 80. A step down transformer 82 is energized via line 80 and is connected to the common line 74, via line 84. The step down transformer 82 is designed to step down the voltage to 6 volts for the purpose of operating the meter relays 32 and 34. The combination of the transformer 82 and the voltage regulator circuitry comprising a zener diode 86, a resistor 88, a capacitor 90 and the diode 92 produce 6 volts DC. The first and second meter relays 32 and 34 are connected in parallel to the 6 volt DC supply. The first meter relay 32 is enabled via line 104. A low voltage light 106 is supplied with 6 volts via line 108. Color sensor 24 comprises a cadmium sulfide element that functions as a variable resistor. The resistance of color sensor 24 varies relative to the color density of light passing through pipe 25. The change in resistance of the color sensor 24 controls the operation of the indicator 112. The first meter relay 32 operates between parameters as set by the potentiometer 114 that is enabled via line 108. When the color density of light passing through the pipe 25 falls below the prescribed parameters as set by the potentiometer 114, the indicator 112 falls outside the preset limits and provides a visual indication that the composition of the etchant is unsatisfactory. Line 116 is the return line back to the 6 volt DC supply. The second meter relay 34 is operative in a similar manner. The color sensor 28 is enabled via line 94, and the indicator 98 is responsive to the varying resistance of the color sensor 28. The potentiometer 100 is enabled via line 102. A second low voltage light 96 is enabled via line 99, the light rays from which, through pipe 31, affect the resistance of the color sensor 24.

The first meter relay 32 maintain a continous monitoring of the color density of the etchant. If the etchant has a satisfactory color density, a switch 118 is in contact with the neutral contact 120. This has the effect of disenabling the apparatus except for the meter relays 32 and 34 that receive low voltage power as previously described. If the first meter relay 32 senses a color density deficiency that causes the indicator 112 to fall outside the prescribed limits, the switch 118 is tripped and makes contact with contact 122. When this happens, a high voltage supply, via line 124, through switch 118, and then through line 126 is present at switch 128 that is part of the system of the second meter relay 34. The second meter relay 34 is preset to be less sensitive than the first meter relay 32. This means that the indicator 98 will cause switch 128 to switch from the neutral contact 129 to the live contact 130 prior to switching the switch 118 to the live contact 122. Therefore, at the time line 126 is energized, the switch 128 is in a position to enable line 132.

Line 132 enables the timer 64. The timer relay 135 is enabled via switch 134 and line 136. The timer 64 is connected to the common line 74 via line 139. If the second meter relay 34 senses a relatively rapid improvement in the color density of the etchant, the indicator 98 causes the switch 128 to make contact with the neutral contact 129 before the timer 64 times out. This removes the power from the timer 64 causing it to have no further effect on the system at that particular time. If however, no change in the color density in the system is sensed prior to the timing out of the timer 64, the relay 135 latches the switch 134 to make contact at 138. Since the switch 134 is biased to make contact at 140, the action of the relay 135 causes a momentary break in the time circuit and causes the switch 134 to momentarily switch to contact 138 after which time it switches back to contact 140. During that momentary contact at 138, it enables line 142 and the relay 144. The relay 144 is connected to the common line via line 146. During the momentary energization of relay 144, it latches switch 148 from either contact 150 or 152 to the other, depending upon the last position of the switch 148. For example, if the switch 148 was making contact at 152, the relay 144 will switch it to make contact at 150. In making contact at 152, motor 44 via pump 52 causes acid to be introduced into the reaction chamber 27. Motor 44 is energized via line 156, switch 148 and line 158. When the switch 148 is making contact at 150, motor 46 via pump 58 causes oxidizer to be introduced into the reaction chamber 27. Motor 46 is energized via line 156, switch 148 and line 160. The motors 44 and 46 are connected to the common line 74 via the lines 162 and 164 respectively. The motors 44 and 46 are alos connected to a ground line 166 via the lines 168 and 170 respectively.

When the second meter relay 34 senses an improvement in the color density of the etchant, the switch 128 is moved to make contact with the neutral contact 129. This has the effect of disenabling the timer 64. Therefore, the apparatus remains in the constituent component mode that is curing the system until such time as the first meter relay 32 senses a change in the color density of the system in which it falls between the predetermined parameters. At such time as the color density improves, the switch 118 is switched over the neutral contact 120 disenabling line 156 that in turn disenables whichever of the motors 44 or 46 that had been in operation. The etching machine 10 continues operation without the addition of acid or oxidizer until such time as the color density falls outside the predetermined parameters. The first meter relay 32 maintains constant vigilance on the system and any time the color density of the etchant becomes unacceptable, it recycles the previously described system. In this next cycle, the switch 148 remains in contact at 150 or 152 depending upon its position in the previous cycle. Therefore, the first component added in the recycling of the system will be that same component that cured the deficiency in the previous cycle. If that component is the proper one to cure the deficiency, the switch 128 will move to neutral contact 129 disenabling the timer 64 and permitting addition of the curing component until the first meter relay 32 senses an improvement in the etchant. If however, that component does not cure the deficiency in the etchant, the timer 64 times out and causes the switch 148 to move to the other position causing the addition of the other component that instigates a cure of the deficiency.

The apparatus that has been disclosed maintains a continuous monitoring of the etchant and cycles on and off as necessary to cure the deficiencies in the etchant. No pH readings are necessary during the operation of the apparatus since the change in the color density is reflective of the change in pH of the etchant. It should also be noted that except during periods when one or the other constituent component is being added to the etchant, the apparatus draws power only through two low voltage meter relays 32 and 34.

Having described my invention, I now claim:

1. A method of automatically monitoring the condition of an etchant in an etching machine and regenerating the same comprising the steps of:
    monitoring the changes in etchant composition to determine the condition of deficiency of the etchant,
    adding a constituent component to regenerate the etchant to a predetermined etching vigor,
    and monitoring the etchant after the addition of the constituent component to determine if the constituent component addition is causing a cure of the deficiency,
    discontinuing the addition of a constituent component if such addition fails to cure the deficiency,
    and adding another constituent component to cure the deficiency.

2. The method of claim 1 wherein:
    the step of monitoring the etchant composition to determine the condition of the deficiency comprises sensing the intensity of light transmitted through the etchant,
    and initiating constituent component addition in the event the light intensity falls outside a predetermined range of intensity parameters.

3. The method of claim 1 wherein:
    the step of monitoring the etchant after the addition comprises sensing the intensity of light transmitted through the etchant after the component addition,
    and the step of discontinuing the component addition when the light intensity falls between the predetermined range of intensity parameters.

4. The method of claim 1 wherein:
    The step of adding a constituent component comprises adding acid to the etchant,
    and the step of adding another constituent component comprising adding oxidizer to the etchant.

5. The method of claim 1 including the steps of:
    detecting flow from the etching machine prior to initiating the monitoring of the etchant step,
    and delaying the monitoring of the etchant step for a predetermined time period after etchant flow is detected.

6. A method of automatically monitoring the condition of an etchant in an etching machine and regenerating the same comprising the steps of:
    monitoring the changes in etchant composition to determine the condition of deficiency of the etchant,
    adding a constituent component to regenerate the etchant to a predetermined etching vigor,
    monitoring the etchant after the addition of the constituent component to determine if the constituent component addition is causing a cure of the deficiency,
    the step of monitoring the etchant after the addition comprises sensing the intensity of light transmitted through the etchant after the component addition,
    discontinuing the component addition when the light intensity falls between the predetermined range of intensity parameters,
    discontinuing component addition, after a given time delay, if the light intensities fail to converge toward the predetermined range of intensity parameters,
    and switching to the addition of another constituent component, such addition continuing until the light intensity falls within the predetermined range of intensity parameters.

7. A method of automatically monitoring the condition of an etchant in an etching machine and regenerating the same comprising the steps of:
    circulating a quantity of etchant along a flow path,
    monitoring at a first position along the flow path the changes in etchant composition to determine the condition of deficiency of the etchant,
    adding a first constituent component to regenerate the etchant to a predetermined etching vigor,
    monitoring the etchant after the addition of the constituent component to determine if the constituent component addition is causing a cure of the defeciency,
    monitoring said etchant downstream of said addition of said first constituent, and
    discontinue the addition of said first constituent upon failure to detect an improvement and initiate the addition of a second constituent component.

8. A method of automatically monitoring the condition of an etchant in an etching machine and regenerating the same comprising the steps of:
    monitoring the changes in etchant composition to determine the condition of deficiency of the etchant,
    alternately adding first and second constituent components to said etchant for predetermined time intervals,
    monitoring the etchant after each addition of a constituent component to determine if the constituent component addition is causing a cure of the deficiency,
    continuing to add the improving etchant upon detection of an improvement until said deficiency is cured.

* * * * *